United States Patent
Bharmi et al.

(10) Patent No.: US 8,600,490 B1
(45) Date of Patent: Dec. 3, 2013

(54) TWO-DIMENSIONAL REFRACTORY PERIOD

(75) Inventors: Rupinder Bharmi, Canyon Country, CA (US); Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 1348 days.

(21) Appl. No.: 11/943,825

(22) Filed: Nov. 21, 2007

(51) Int. Cl.
*A61B 5/04* (2006.01)

(52) U.S. Cl.
USPC ........... 600/517; 600/509; 600/516; 600/521; 607/9; 607/27

(58) Field of Classification Search
USPC ................. 607/9, 27; 600/521, 509, 516, 517
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,466,254 A | 11/1995 | Helland | |
| 5,476,483 A | 12/1995 | Bornzin et al. | |
| 5,891,048 A * | 4/1999 | Nigam et al. | 600/521 |
| 6,266,565 B1 * | 7/2001 | Er et al. | 607/27 |
| 6,539,259 B1 * | 3/2003 | Weinberg et al. | 607/9 |
| 6,944,499 B2 | 9/2005 | Tang et al. | |
| 2004/0015197 A1 * | 1/2004 | Gunderson | 607/27 |
| 2004/0127947 A1 * | 7/2004 | Kim et al. | 607/9 |
| 2004/0243014 A1 * | 12/2004 | Lee et al. | 600/510 |
| 2005/0245976 A1 * | 11/2005 | Wang | 607/9 |

OTHER PUBLICATIONS

Barold, S. et al, "Cardiac Pacemakers Step by Step, An Illustrated Guide," (c) 2004, Futura, an imprint of Blackwell Publishing; pp. 92 and 259.

* cited by examiner

*Primary Examiner* — Christopher D Koharski
*Assistant Examiner* — Natasha Patel

(57) ABSTRACT

A two-dimensional refractory period is defined in conjunction with the detection of cardiac events. Detection parameters associated with the two-dimensional refractory period may define a period of time during which a sensed cardiac signal is blanked or may define a period of time during which a given sensing threshold applies. The two-dimensional refractory period may be employed in atrial sensing to selectively blank far-field T-waves while enabling P-wave detection. The two-dimensional refractory period may be employed in ventricular sensing to selectively blank near-field T-waves while enabling detection of the QRS complex. The detection parameters associated with the two-dimensional refractory period may be adapted based on characteristics of previously detected cardiac signals.

14 Claims, 8 Drawing Sheets

TWO-DIMENSIONAL REFRACTORY PERIOD

TECHNICAL FIELD

This application relates generally to a cardiac device and more specifically, but not exclusively, to a two-dimensional refractory period for an implantable cardiac rhythm management device.

BACKGROUND

Implantable medical devices, such as implantable cardiac rhythm management devices (e.g., pacemakers, defibrillators, and cardioverters), monitor and provide therapy to the heart of a patient that suffers from a cardiac arrhythmia. For example, in an attempt to maintain regular rhythm, an implantable device may track the type and timing of native cardiac signals generated by the heart. In this way the implantable device may determine whether cardiac events (e.g., contractions) are occurring and whether they are occurring at the proper times. In the event contractions are not occurring or are occurring at undesirable times, the implantable device may stimulate the heart in an attempt to restore proper rhythm. For example, an implantable device may stimulate the cardiac muscles of one or more of the chambers of the heart by delivering electrical pulses via one or more leads implanted in or near the chamber(s).

An implantable device also may track cardiac signals via one or more leads that are implanted in or near one or more of the chambers of the heart. Here, through the use of amplification, threshold detection and filtering, signals received via the leads may be associated with a particular cardiac event. These cardiac events may include, for example, P-waves, R-waves, and T-waves. A P-wave corresponds to a contraction (depolarization) of an atrium. A QRS complex (comprising an R-wave) corresponds to a contraction (depolarization) of a ventricle. A T-wave corresponds to a return to a resting state (repolarization) of a ventricle.

In some implementations an implantable device may employ a sense amplifier and a threshold detector for cardiac event detection. In some aspects, the sense amplifier senses cardiac signals and provides the sensed signals to the threshold detector.

The sense amplifier may include or be associated with a signal filter. Here, the bandwidth of the filter may be selected to allow the signals that the system is attempting to detect to pass through the filter. In general, the filter is designed in a manner that tends to reject any other signals. That is, other signals that are not of interest may not pass through the filter or may be significantly attenuated by the filter.

The signals that pass through the filter may be provided to the threshold detector. The threshold detector generates an output signal in the event the amplitude of the input signal exceeds a fixed threshold level or a threshold level defined by an automatic sensitivity control scheme. The output signal may thus be taken as an indication that a certain cardiac event has occurred. The output by the threshold detector may thus indicate detection of a P-wave, an R-wave, or some other signal.

By analyzing the type and timing of these indications the implantable device may determine whether stimulation pulses need to be generated as noted above. Thus, if the implantable device detects cardiac events at the appropriate relative times, the device may simply continue monitoring the received indications. In contrast, if an indication has not been received for a predefined period of time, the implantable device may deliver an appropriate stimulation (e.g., pacing) pulse to the heart. Alternatively, in the event a tachycardia condition is detected, the implantable device may deliver a stimulation shock to the heart.

In some aspects, the accuracy with which an implantable device identifies cardiac events may depend on appropriate programming of atrial and ventricular sensitivities as well as refractory and blanking periods. For example, for atrial sensing a post-ventricular atrial refractory period ("PVARP") may be employed to avoid inappropriate sensing of retrograde conducted P-waves. In addition, a post-ventricular atrial blanking ("PVAB") period may be employed to prevent over sensing of far-field QRS complexes and to improve detection of atrial fibrillation. Here, sensed atrial events that fall within the PVAB period may be ignored by, for example, a mode switch algorithm that monitors the peak-to-peak interval in an atrial refractory period (PVARP or AV-PV delay) to trigger a mode switch when atrial fibrillation is detected. Also, a pre-ventricular atrial blanking ("PREVAB") period may be used to improve far-field R-wave discrimination. For ventricular sensing, a ventricular refractory period ("VREF") may be employed to avoid double-counting of ventricular depolarization and repolarization (e.g., QRS complexes and T-waves, respectively).

Techniques such as those described above may not always provide a proper indication of cardiac events. For example, a P-wave detection circuit may indicate a detection based on a true P-wave in some instances while, in other instances, the circuit may improperly indicate a detection in response to reception of a far-field R-wave, a far-field T-wave, extracardiac physiologic noise, or external noise. Similarly, an R-wave detection circuit may indicate a true R-wave in some instances and, in other instances, improperly indicate a detection in response to reception of a T-wave, redetection of the same R-wave, or noise. Thus, in practice, the selection of appropriate sensitivity thresholds and blanking periods may involve a complex trade-off between P-wave sensing performance, atrial fibrillation sensing performance, and far-field oversensing.

SUMMARY

A summary of several sample aspects of the disclosure follows. For convenience, one or more aspects of the disclosure may be referred to herein simply as "some aspects."

The disclosure relates in some aspects to detection of cardiac events. In particular, sensed cardiac signals are processed in a manner that facilitates detection of events of interest in the cardiac signals while reducing the likelihood of detection of cardiac events that are not of interest.

The disclosure relates in some aspects to a two-dimensional refractory period for detecting cardiac events. Here, detection parameters such as time periods and sensing parameters employed during these time periods may be independently adapted to provide improved detection performance. In some aspects the sensing parameters relate to rejecting (e.g., blanking) certain types of cardiac signals that fall below a given threshold while passing other types of cardiac signals that exceed the threshold. Thus, in some aspects adaptation of the two-dimensional refractory period may involve selecting a period of time during which a given sensing threshold applies. In addition, adaptation of the two-dimensional refractory period may involve selecting a period of time during which a sensed cardiac signal is blanked.

A two-dimensional refractory period may be employed in atrial sensing to selectively blank far-field T-waves while enabling P-wave detection. Here, an atrial detection threshold and the time period during which that threshold is used may be selected to provide improved sensitivity for detection of events such as atrial fibrillation and retrograde P-waves, while reducing the possibility of inadvertently identifying far-field T-waves as P-waves.

Similarly, a two-dimensional refractory period may be employed in ventricular sensing to selectively blank T-waves while enabling R-wave detection. Here, improved sensitivity may be provided for detection of events such as ventricular fibrillation, while reducing the possibility of inadvertently identifying T-waves as R-waves.

In some aspects a two-dimensional refractory period is adapted based on characteristics of previously sensed cardiac signals. For example, characteristics of the previously sensed signals such as the relative timing of a certain type of event and the relative magnitude of that event may be tracked over time. Based on this historical information, each dimension of the two-dimensional refractory period may be adjusted as necessary to effectively detect or reject that event while also attempting to maintain effective detection or rejection of other events. Similar operations may be performed for other cardiac events. In addition, these operations may be performed on a repeated basis in an attempt to continually provide a desired level of detection performance.

BRIEF DESCRIPTION OF THE DRAWINGS

These and other features, aspects, and advantages will be more fully understood when considered with respect to the following detailed description, the appended claims, and the accompanying drawings, wherein:

Figure 1:
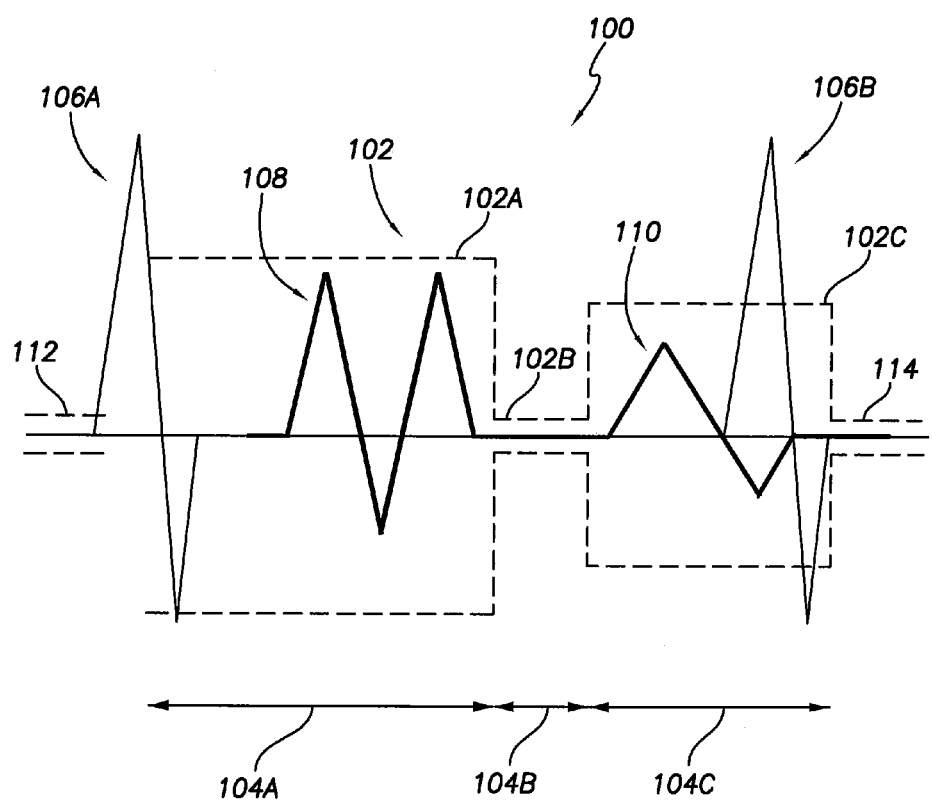
FIG. 1 is a simplified timing diagram of an embodiment of a two-dimensional refractory period.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

One aspect of cardiac rhythm management relates to sensing cardiac signals to determine whether therapy should be applied and, if so, the type of therapy to be applied. In some aspects, this sensing operation involves distinguishing different types of cardiac signals that are acquired by a sense circuit. Such signals may relate to, for example, P-waves, QRS complexes, T-waves, premature atrial contractions ("PACs"), premature ventricular contractions ("PVCs"), arrhythmias, or other cardiac events. Here, it may be desirable to distinguish between events that occurred in a given channel from events associated with far-field signals so that appropriate therapy may be administered. For example, when sensing in the atrium a sensing circuit may be configured to distinguish between a P-wave and a far-field T-wave.

The following disclosure relates in some aspects to selectively detecting cardiac signals of interest while ignoring cardiac signals that are not of interest, based on the characteristics of each of these signals. For example, through the use of a two-dimensional refractory period, a cardiac rhythm management device may selectively blank T-waves while enabling detection of P-waves.

Referring to FIG. 1, a timing diagram 100 illustrates, in a simplified manner, an embodiment of a two-dimensional refractory period defined for an atrial channel. The two-dimensional refractory period is generally represented by dashed line 102.

In some implementations the two dimensions of the refractory period 102 relate to time and to one or more sensitivity thresholds (e.g., amplitudes). For example, in FIG. 1 the refractory period 102 defines several distinct time periods, each of which may be associated with a different sensitivity threshold. In this example, first, second, and third time periods of the refractory period 102 correspond to periods of time represented by arrows 104A, 104B, and 104C, respectively. In addition, the relative vertical positions of line segments 102A, 102B, and 102C associated with the time periods 104A, 104B, and 104C indicate the relative magnitude of the sensitivity threshold associated with each time period.

FIG. 1 also illustrates that different portions of the refractory period 102 may be defined relative to one or more events that may be sensed in a cardiac channel. For example, the beginning of the refractory period 102 may be defined to coincide with detection of a P-wave 106A while one or more of the time periods 104A, 104B, and 104C may be associated with cardiac events (e.g., a far-field QRS complex 108 or a far-field T-wave 110) that may be sensed in the atrial channel.

Figure 2:
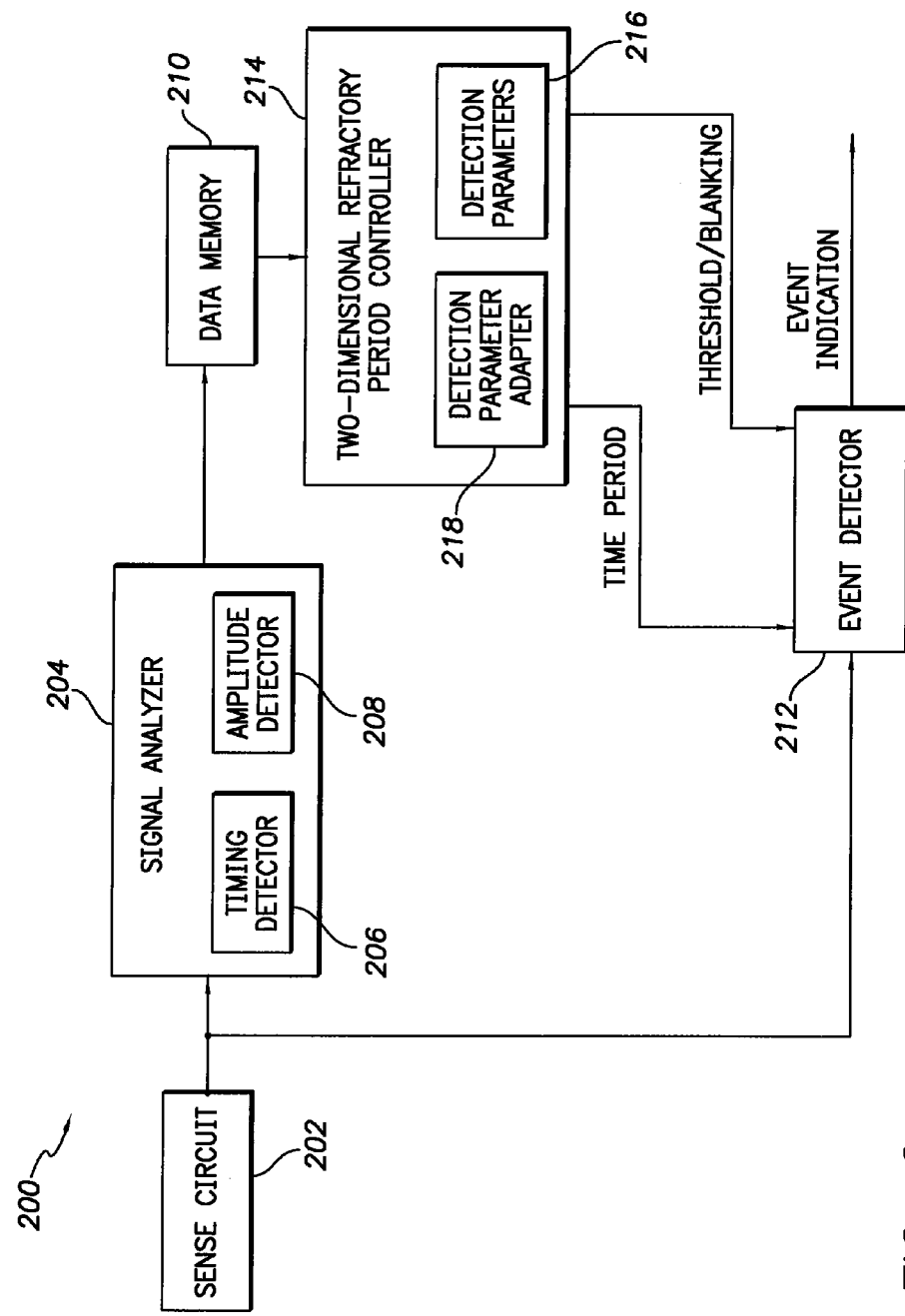
FIG. 2 is a simplified block diagram of an embodiment of a system for defining and using a two-dimensional refractory period.
Figure 3:
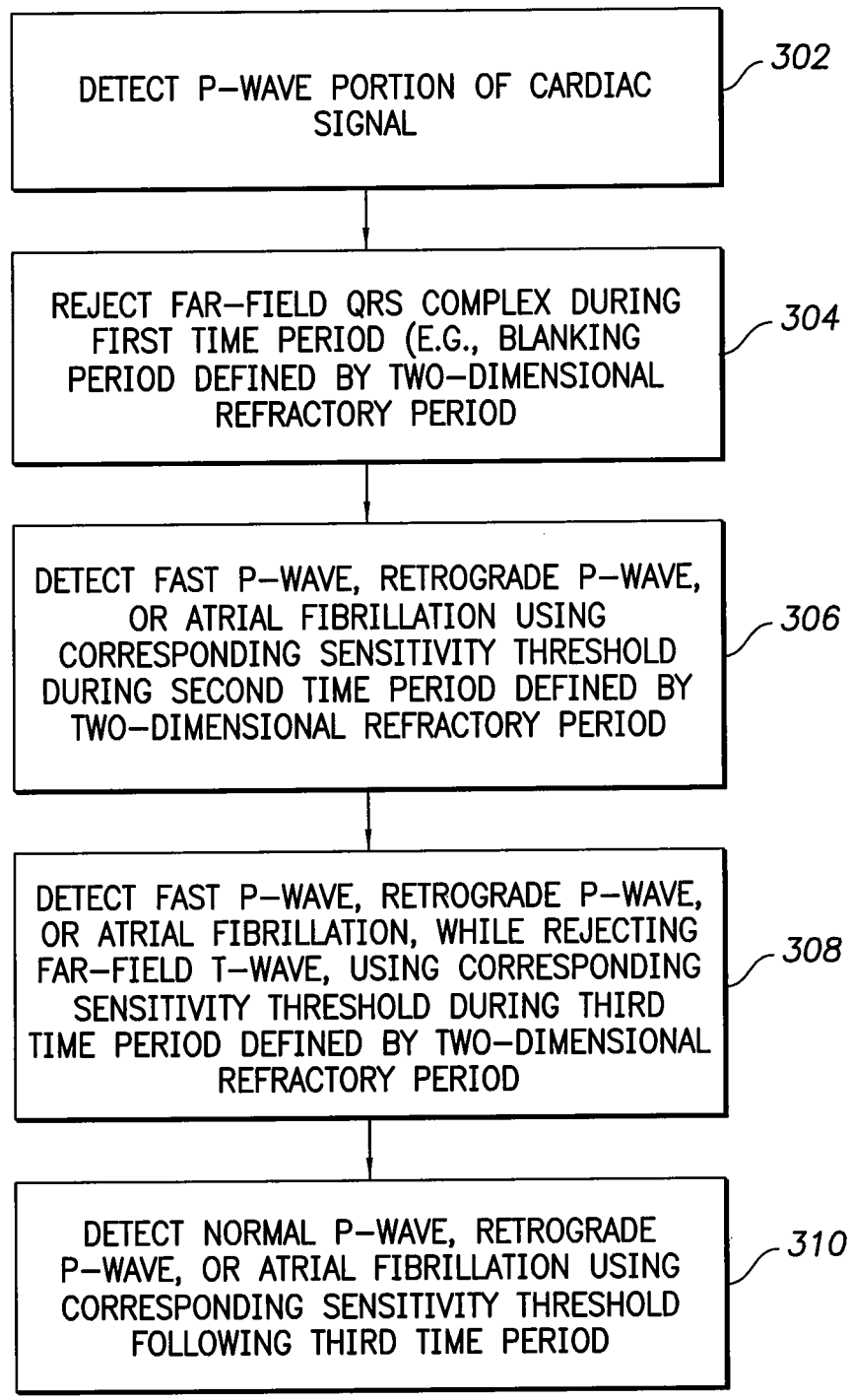
FIG. 3 is a simplified flowchart of an embodiment of operations that may be performed in conjunction with detecting cardiac events in an atrial channel using a two-dimensional refractory period.

For purposes of illustration, sample operations relating to cardiac signal detection based on a two-dimensional refractory period will described in conjunction with a cardiac system 200 that may be implemented in a cardiac device as shown in FIG. 2 and an operational flowchart as shown in FIG. 3.

The system 200 includes a sense circuit 202 for sensing cardiac signals. As will be discussed in more detail in conjunction with FIGS. 8 and 9 below, the sense circuit 202 may include or operate in conjunction with one or more implantable leads and include appropriate amplification and filtering components to repeatedly provide cardiac signals corresponding to each cardiac cycle.

The system 200 also includes several components 204-210 that may be employed in conjunction with defining a two-dimensional refractory period based on sensed cardiac signals. Sample operations of these components will be treated in more detail in conjunction with FIG. 4.

Finally, the system 200 includes an event detector component 212 that cooperates with a two-dimensional refractory period controller 214 to detect events associated with the sensed cardiac signals using the two-dimensional refractory period. For example, the controller 214 may define detection parameters 216 that are representative of the two-dimensional refractory period and provide these parameters to the component 212. As discussed below in conjunction with FIG. 3, these detection parameters may include time period information and detection threshold-related information that define when and how certain detection operations are to be performed.

FIG. 3 illustrates several sample detection operations that may be performed by a cardiac device. For convenience, the operations of FIG. 3 (or any other operations discussed or taught herein) may be described as being performed by specific components (e.g., the components of FIG. 2). It should be appreciated, however, that these operations may be performed by other types of components and may be performed using a different number of components. It also should be appreciated that one or more of the operations described herein may not be employed in a given implementation.

As represented by block 302 of FIG. 3, during a typical cardiac cycle the system 200 will detect a P-wave associated with depolarization of the atria. To this end, the system 200 includes a sense circuit 202 (FIG. 2) that may be configured to sense cardiac signals in the atrial channel. In conjunction with this sensing, the event detector 212 may be configured to detect signals that, for example, exceed a given threshold level such as a noise floor (e.g., as represented by the dashed line 112 in FIG. 1). Additional components that may be implemented in or in conjunction with the sense circuit 202 and/or the event detector 216 are treated below conjunction with FIGS. 8 and 9.

After detection of the P-wave 106A by the event detector 212, the event detector 212 will commence detection of events associated with cardiac signals that are sensed during the remainder of the cardiac cycle. In accordance with the teachings here, this detection may be based on a two-dimensional refractory period.

As represented by block 304 of FIG. 3, the first time period 104A may be defined to prevent detection of a far-field QRS complex. Accordingly, as will be discussed in more detail below in conjunction with FIG. 4, the starting and ending times (e.g., the duration) of the first time period 104A may be defined based on the expected durations of far-field QRS complexes that may be detected in the atrial channel. In addition, a sensitivity threshold of the first time period 104A as represented by corresponding upper and lower boundaries in FIG. 1 (e.g., line segment 102A) may be defined based on the expected magnitudes of these far-field QRS complexes.

In some implementations the first time period 104A may be defined as a blanking period. Accordingly, in these cases the sensitivity threshold for the first time period 104A may simply indicate that no detection is to occur during this time period.

As represented by block 306 of FIG. 3, the second time period 104B corresponds to a period of time associated with, for example, a low probability of detection of regular signals in the atrial channel. For example, based on analysis a previously received cardiac signals a determination may be made that it is unlikely that any far-field QRS complexes or far-field T-waves will be detectable in the atrial channel during this time period. The starting and ending times of the second time period 104B may thus be defined based on the expected timing of such far-field signals (e.g., defined as the period of time between such signals). In addition, a sensitivity threshold of the second time period 104B as represented by the corresponding upper and lower boundaries (e.g., line segment 102B) may be defined just above the noise floor of the atrial channel or in some other manner to increase the sensitivity of the detection during this time. In this way, the cardiac rhythm management device may more effectively detect P-waves (e.g., early P-waves or retrograde P-waves), PACs, any cardiac signals that may indicate atrial fibrillation, or any other signals of interest.

As represented by block 308, the third time period 104C is defined to reject a far-field T-wave (e.g., prevent detection of at least a portion of the far-field T-wave) while enabling detection of a P-wave 106B. For example, under certain circumstances (e.g., during high atrial rates) a fast P-wave may appear in the atrial channel at about the same time as the far-field T-wave. To provide the desired signal detection and rejection, the starting and ending times of the third time period 104C may be defined based on the expected timing and durations of any far-field T-waves. In addition, a sensitivity threshold of the third time period 104C as represented by the corresponding upper and lower boundaries (e.g., line segment 102C) may be defined based on the expected magnitudes of the far-field T-waves and/or the expected magnitudes of the P-waves or some other signals of interest. In particular, the sensitivity threshold may be set above the expected magnitudes of the far-field T-waves and below the expected magnitudes of the P-waves (e.g., fast P-waves or retrograde P-waves), PACs, arrhythmia signals, etc., to provide the above-mentioned selectivity. Accordingly, through the use of a two-dimensional refractory period, more effective sensing may be achieved as compared to conventional techniques that simply employ blanking periods during the time a far-field T-wave is expected to appear in the atrial channel.

As represented by block 310, in the event a P-wave was not detected during the third time period 104C (i.e., the P-wave 106B was not present), the event detector 212 may continue its detection operations. For example, the cardiac device may revert to normal atrial sensing (e.g., using a fixed threshold or automatic sensitivity control). Thus, a lower sensitivity threshold may be employed to enable more effective detection of normal P-waves, retrograde P-waves, PACs, any cardiac signals that may indicate atrial fibrillation, or any other signals of interest. An example of such a lower sensitivity threshold is represented by upper and lower boundaries of the illustrated dashed line (e.g., line segment 114). As mentioned above, this threshold may be defined just above the noise floor of the atrial channel or in some other manner to increase the sensitivity of the detection during this time. Here, it should be appreciated that the continuation of these detection operations may correspond, in the following cardiac cycle, to the detection operations that precede the P-wave 106A of FIG. 1 (e.g., corresponding to the dashed line 112).

From the above it should be appreciated that in contrast with some conventional techniques that may simply ignore signals from a sense circuit during certain portions of the atrial refractory period, a cardiac device constructed in accordance with the teachings herein may be selectively alert through the use of an alternate sense threshold. As will be discussed in more detail in conjunction with FIG. 4, this alternate threshold may be fixed or may be variable and, in some implementations, may be set automatically by the cardiac device based on, for example, cardiac signals (e.g., far-field signals) sensed by the sense circuit.

As illustrated by FIG. 1, the alternate threshold may be set above the amplitude of the far-field T-wave 110 so that the far-field T-wave may be ignored while a larger P-wave 106B may still be detected. Consequently, through the use of the two-dimensional refractory period, a cardiac device may be configured to be more sensitive to P-waves and atrial fibrillation and less sensitive to far-field signals. In addition, the cardiac device may be configured to be more sensitive to other atrial signal such as retrograde P-waves. In some implementations, additional morphological markers may be used to distinguish between native P-waves and retrograde events such that the refractory period may correctly cover (e.g., blank) the retrograde events, and not the native P-waves. Through the use of the above techniques, the cardiac device may acquire more relevant information to determine the appropriate therapy for a given cardiac cycle. For example, certain events detected during the time periods 102B and 102C may be added to a filtered atrial rate interval counter to enable the cardiac device to mode switch or act on a fast event or a retrograde event.

Also, through the use of a two-dimensional refractory period, a cardiac device may not need to employ separate post ventricular atrial blanking ("PVAB"). Rather, in some implementations this functionality may be provided by the two-dimensional refractory period (e.g., at time period 104A in FIG. 1).

Figure 4:
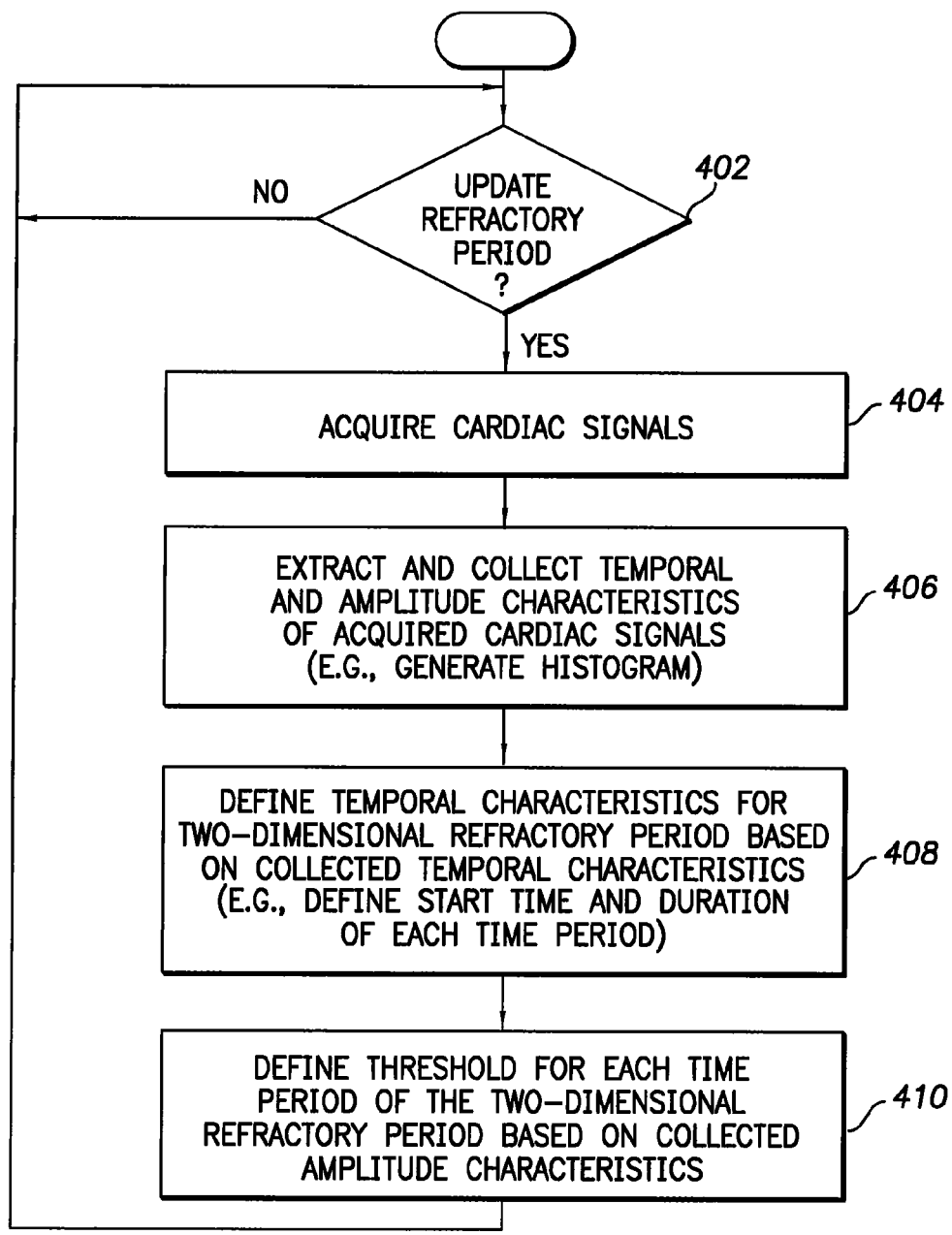
FIG. 4 is a simplified flowchart of an embodiment of operations that may be performed to define a two-dimensional refractory period.

FIG. 4 illustrates an embodiment of operations that may be performed to define (e.g., update) a two-dimensional refractory period. In particular, these operations involve acquiring and analyzing cardiac signals to identify time periods during which certain types of cardiac events may be expected to occur and to identify amplitude levels of these events so that appropriate sensitivity thresholds may be defined for the two-dimensional refractory period.

For illustration purposes, the operations of FIG. 4 will be discussed in the context of being performed by various components of the system 200 of FIG. 2. It should be appreciated, however, that the illustrated components of the system 200 are merely representative of components that may be employed here and that one or more of the operations of FIG. 4 may be performed by or in conjunction with other suitable components.

As represented by block 402, at some point in time the system 200 may commence operations to define (e.g., update) a two-dimensional refractory period. For example, in some implementations the system 200 may perform these operations on a regular basis (e.g., periodically such as once a week, or at other times).

As represented by block 404, the system 200 acquires cardiac signals that will be used to define a two-dimensional refractory period. In some implementations cardiac signals may be acquired on a continual basis by an implantable cardiac device for use in pacing or other operations. Here, the implantable cardiac device may digitize cardiac signals sensed by the sense circuit 202 and store the resulting intracardiac electrogram ("IEGM") data in a data memory for subsequent use. Consequently, in these cases the acquisition of the cardiac signals at block 404 may simply involve retrieving IEGM data from a data memory.

As represented by block 406, a signal analyzer 204 may analyze the acquired cardiac signals to distinguish different types of cardiac signals in terms of location, amplitude, and morphology. For example, the signal analyzer 204 may identify the occurrence of P-waves, fast P-waves, retrograde P-waves, PACs, arrhythmia signals, far-field QRS complexes, far-field T-waves, and other events that are sensed in the atrial channel. In addition, the signal analyzer 204 may comprise a timing detector 206 and an amplitude detector 208 for determining the timing and amplitude, respectively, of the identified cardiac signals. The signal analyzer 204 may then store this information in a data memory 210 for subsequent use in conjunction with discriminating between these signals and defining the refractory period.

In some implementations the signal analyzer 204 comprises a histogram generator that generates a histogram based on the timing and amplitude information of the acquired cardiac signals. For example, the histogram generator may collect data relating to the statistical prevalence of cardiac events in the atrial channel (or, as discussed below, in the ventricular channel).

Here, timing of certain events such as far-field signals may be based on the predictability of the timing of these events. For example, true far-field signals in the atrial channel will tend to be repeatable in their timing relationship with respect to the corresponding ventricular event while atrial events will not tend to have a strong time correlation with those ventricular events. Conversely, in the ventricular channel, near-field signals tend to be repeatable in their timing relationship with respect to the preceding ventricular event.

Thus, in some embodiments the histogram generator may establish a plurality of successive time windows relative in time to a ventricular event. Detected events sensed over a plurality of cardiac cycles (e.g., where detection of an event is indicated by a transition through a threshold) are assigned to time windows corresponding in time to the time of detection. Consequently, a corresponding sensing time period for such events may be defined in the two-dimensional refractory period based on the number of detected events associated with each of the time windows.

Figure 5:
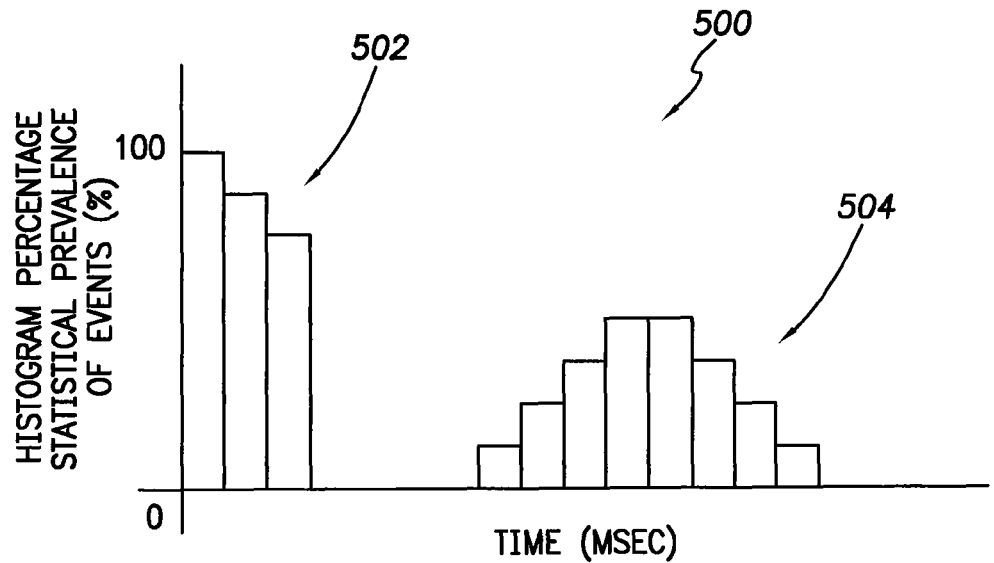
FIG. 5 is a simplified diagram of an embodiment of histogram data.

FIG. 5 illustrates, in a simplified manner, histogram information 500 relating to cardiac signals that may be acquired over a series of cardiac cycles. As mentioned above, the histogram includes a plurality of successive time windows. The time windows (or bins) begin a defined time after detection of an R-wave (e.g., 100 ms). In the example of FIG. 5, the histogram generator has collected a first set of data 502 near the beginning of the cardiac cycle that relates to the statistical prevalence of sensed far-field QRS complexes (e.g., R-waves). In addition, the histogram generator has collected a second set of data 504 appearing at a later point in the cardiac cycle that relates to the statistical prevalence of sensed far-field T-waves.

The width of the time windows may depend on the desired specificity of the timing information. As an example, in some implementations a time window may be 8 milliseconds wide.

It should be appreciated that such histogram data may take various forms. For example, in some implementations the histogram generator may maintain samples (e.g., based on an 8 millisecond bin) of T-wave means and standard deviations over the entire width of the T-wave. In addition, in some implementations the histogram generator may maintain T-wave maximum and minimum running averages. In some implementations the histogram generator may maintain T-wave ensemble average profiles with standard deviations over time.

Referring again to FIG. 4, at blocks 408 and 410 the refractory period controller 214 (e.g., a detection parameter adapter 218) adapts the detection parameters 216 (e.g., temporal characteristics and amplitude characteristics) for the two-dimensional refractory period based on the data collected over a given number of cardiac cycles at block 406. For example, at block 408 the adapter 218 may define one or more time periods (e.g., time periods 104A and 104C in FIG. 1) for the refractory period based on the temporal characteristics collected at block 406 for a far-field QRS complex and a far-field T-wave. Similarly, at block 410 the adapter 218 may define one or more sensitivity thresholds (e.g., as represented by line segments 102A and 102C in FIG. 1) for one or more time periods of the refractory period based on the far-field QRS and T-wave amplitude characteristics collected a block 406.

In some aspects the length of the refractory period defined at block 408 may be based on the temporal relationship of the near-field or far-field repolarization event versus the depolarization event. For example, for an atrial channel the overall length of the refractory period may relate to the time duration between a P-wave and a far-field T-wave. Conversely, for a ventricular channel (discussed below) the overall length of the refractory period may relate to the time duration between a QRS complex (e.g., an R-wave) and a near-field T-wave.

In addition, the timing (e.g., start time, end time, duration) of each time period defined for the refractory period may be based on historical data collected at block 406. For example, the width of the time period 104A of FIG. 1 may correspond to the data 502 of FIG. 5. Similarly, the width of the time period 104C of FIG. 1 may correspond to the data 504 of FIG. 5. Thus, the location and durations of each of the time periods of the refractory period may be based on temporal characteristics of the far-field QRS complexes, the far-field T-waves, or some other events that have been detected over a number of cardiac cycles.

At block 410, the sensitivity threshold for each time period defined within the refractory period also may be based on historical data collected at block 406. For example, the height of the time period 104A of FIG. 1 (corresponding to line segment 102A) may correspond to the data 502 of FIG. 5. Similarly, the height of the time period 104C of FIG. 1 (corresponding to line segment 102C) may correspond to the data 504 of FIG. 5. In other words, the sensitivity threshold of the refractory period associated with time period 104C may be based on amplitude characteristics of the far-field T-waves that have been detected over a number of cardiac cycles.

The two-dimensional refractory period may thus be profiled over an ensemble average of an event of interest to provide highly effective event discrimination. Referring again to the example of FIG. 1, for an atrial channel a two-dimensional refractory period associated with the time period 104C may be profiled over a T-wave ensemble average to provide a morphological difference between P-waves and far-field T-waves.

By repeatedly collecting the above information over time to determine the current temporal and amplitude characteristics of the acquired cardiac signals, a cardiac device may automatically define (e.g., adjust) the time periods of the refractory period and any sensitivity thresholds associated with these time periods. In other words, the two-dimensional refractory period may be continually adapted based on how the underlying cardiac signals (e.g., far-field signals) are changing. For example, the width of time period 104A may be widened in the event it is determined that the width of the detected QRS complexes are widening (e.g., due to exacerbation of heart failure). Moreover, this decision may be made in a manner that keeps this time period as short as possible to maximize sensing during the remainder of the refractory period and/or to avoid defining too long of a refractory period (e.g., to prevent unduly limiting the maximum tracking rate). In a similar manner, the height of the threshold associated with line segment 102C may be adjusted up or down based on any detected change in the amplitude of the far-field T-waves (e.g., due to a change in conditions relating to sensing via an implanted sensing lead). As discussed above, these adaptations may be based on statistical analysis of where the corresponding event amplitudes are appearing over a period of time (e.g., in a histogram). Based on this adaptation, the two-dimensional refractory period may be used, for example, to selectively blank certain cardiac events (e.g., QRS complexes and T-waves), while selectively enabling detection of other cardiac events (e.g., a fast P-wave).

It should be appreciated that a two-dimensional refractory period as taught herein may be implemented in a variety of ways. For example, in some implementations a two-dimensional refractory period may be defined to commence after ventricular depolarization. Accordingly, such a refractory period may be referred to as a two-dimensional post ventricular atrial refractory period ("PVARP").

In addition, in some implementations two-dimensional post ventricular atrial blanking ("PVAB") similar to the two-dimensional PVARP may be used in conjunction with a conventional PVARP. This approach may be employed, for example, for patients that experience retrograde P-waves that are preferably managed using a conventional PVARP. Here, correct setting of the blanking period may prevent far-field events from being inappropriately added into the filtered atrial rate. This, in turn, may result in a reduction in false-positive mode switch rates.

As mentioned above, in some implementations a two-dimensional refractory period may be defined for a ventricular channel. The two-dimensional ventricular refractory period may be used, for example, to prevent T-wave oversensing while allowing larger R-waves or other signals to be sensed during the relevant portion of the ventricular refractory period.

In general, the two-dimensional ventricular refractory period may be defined and used in a similar manner as the atrial refractory period described above. For example, the ventricular refractory period may be defined by acquiring cardiac signals from a ventricular channel via the sense circuit 202. Here, the signal analyzer 204 may identify the occurrence of QRS complexes, PVCs, arrhythmia-related signals, near-field T-waves, and other events that are sensed in the ventricular channel. The histogram generator may thus collect data relating to the statistical prevalence of these cardiac events (e.g., in particular near-field T-waves) in the ventricular channel. Based on the temporal and amplitude characteristics of these events (e.g., histogram data) the refractory period controller 214 (e.g., the detection parameter adapter 218) may define detection parameters 216 (e.g., time periods and sensitivity thresholds) for the ventricular refractory period. A sample use of a two-dimensional ventricular refractory period will be discussed in conjunction with FIGS. 6 and 7.

Figure 6:
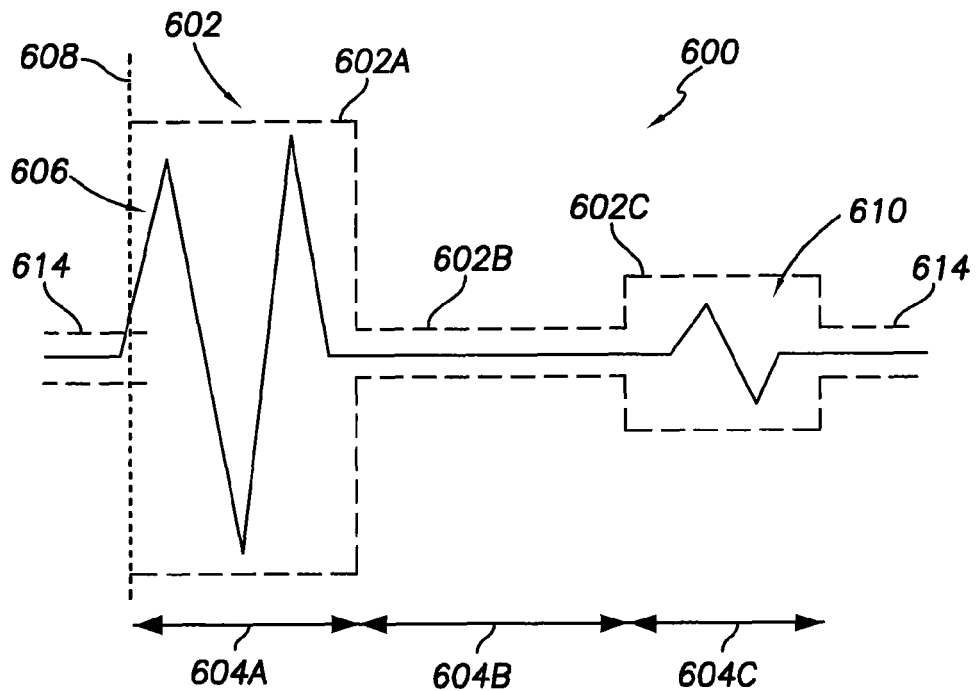
FIG. 6 is a simplified timing diagram of an embodiment of a two-dimensional refractory period for a ventricular channel.

Referring initially to FIG. 6, a timing diagram 600 illustrates, in a simplified manner, an embodiment of a two-dimensional refractory period defined for a ventricular channel. The two-dimensional refractory period is generally represented by dashed line 602.

Again, the two dimensions of the refractory period may relate to time and to one or more sensitivity thresholds. For example, in FIG. 6 the refractory period 602 defines several distinct time periods, each of which may be associated with a different sensitivity threshold. In this example, first, second, and third time periods of the refractory period 602 correspond to periods of time represented by arrows 604A, 604B, and 604C, respectively. In addition, the relative vertical positions of line segments 602A, 602B, and 602C associated with the time periods 604A, 604B, and 604C indicate the relative magnitude of the sensitivity threshold associated with each time period.

FIG. 6 also illustrates that different portions of the refractory period 602 may be defined relative to one or more events that may be sensed in the ventricular channel. For example, the beginning of the refractory period 602 may be defined to coincide with initial detection of a QRS complex 606 while one or more of the time periods 604A, 604B, and 604C may be associated with cardiac events (e.g., a QRS complex 606 or a T-wave 610) that may be sensed in the ventricular channel.

Figure 7:
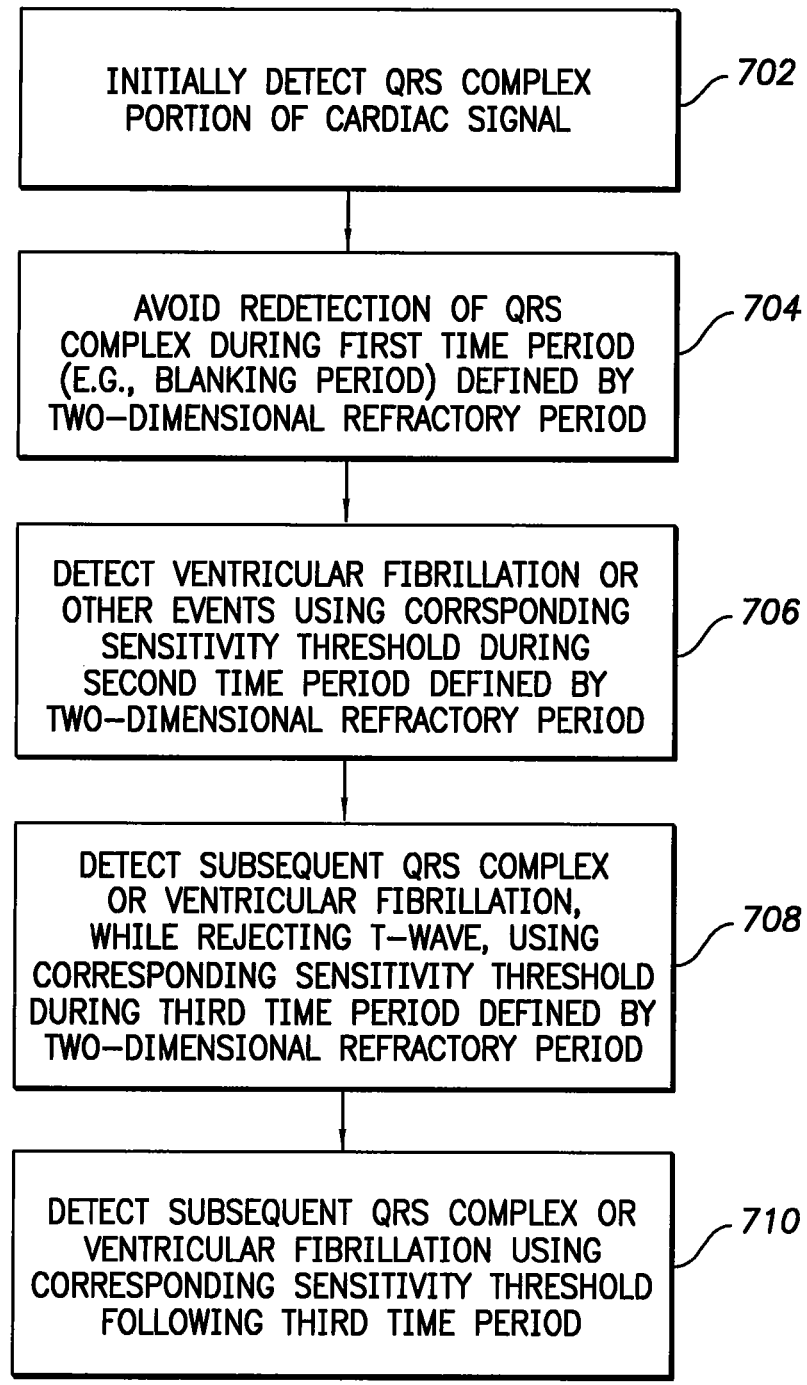
FIG. 7 is a simplified flowchart of an embodiment of operations that may be performed in conjunction with detecting cardiac events in a ventricular channel using a two-dimensional refractory period.

FIG. 7 illustrates an embodiment of ventricular channel detection-related operations. These operations may be similar to the operations discussed above in conjunction with FIG. 2, with the exception that the operations of FIG. 7 relate to sensing events in a ventricular channel. For purposes of illustration, the operations of FIG. 7 also will be described in conjunction with the system 200 of FIG. 2.

As represented by block 702, during a cardiac cycle the system 200 detects a QRS complex (e.g., an R-wave) associated with depolarization of the ventricles. In conjunction with this sensing, the event detector 216 may be configured to detect signals that, for example, exceed a given threshold level such as a noise floor (e.g., as represented by dashed line 612).

After the initial detection of the QRS complex 602 by the event detector 212 (e.g., at a point in time represented by vertical dotted line 608), the event detector 212 will commence detection of events associated with cardiac signals that are sensed in the remainder of the cardiac cycle. In accordance with the teachings here, this detection may be based on a two-dimensional refractory period as represented by the dashed line 602.

At block 704 of FIG. 7, the first time period 604A is defined to prevent redetection of the QRS complex. Thus, the starting and ending times (e.g., the duration) of the first time period 604A may be defined based on the expected durations of QRS complexes that may be detected in the ventricular channel. In addition, a sensitivity threshold of the first time period 604A as represented by the corresponding upper and lower boundaries (e.g., line segment 602A) may be defined based on the expected magnitudes of these QRS complexes.

In some implementations the first time period 604A may be defined as a blanking period. Accordingly, in these cases the sensitivity threshold for the first time period 604A may simply indicate that no detection is to occur during this time period.

At block 706, the second time period 604B corresponds to a period of time associated with, for example, a low probability of detection of regular signals in the ventricular channel. For example, based on analysis a previously received cardiac signals a determination may be made that it is unlikely that any normal QRS complexes or T-waves will be detectable in the ventricular channel during this time period. The starting and ending times of the second time period 604B may thus be defined based on the expected timing of such signals (e.g., defined between such signals). In addition, a sensitivity threshold of the second time period 604B as represented by the corresponding upper and lower boundaries (e.g., line segment 602B) may be defined just above the noise floor of the ventricular channel or in some other manner to increase the sensitivity of the detection during this time. In this way, the cardiac rhythm management device may more effectively detect PVCs, any cardiac signals that may indicate ventricular fibrillation, or any other signals of interest.

As represented by block 708, the third time period 604C is defined to reject a near-field T-wave (e.g., prevent detection of at least a portion of the near-field T-wave) while enabling detection of a QRS complex or any other signals of interest. For example, under certain circumstances a signal of interest (not shown in FIG. 6) may appear in the ventricular channel at about the same time as the near-field T-wave. To provide the desired signal detection and rejection, the starting and ending times of the third time period 604C may be defined based on the expected durations of any near-field T-waves. In addition, a sensitivity threshold of the third time period 604C as represented by the corresponding upper and lower boundaries (e.g., line segment 602C) may be defined based on the expected magnitudes of the near-field T-waves and/or the expected magnitudes of QRS complexes or some other signals of interest. In particular, the sensitivity threshold may be adapted to be set above the expected magnitudes of the near-field T-waves and below the expected magnitudes of the QRS complexes to provide the above-mentioned selectivity. Accordingly, through the use of a two-dimensional refractory period, more effective sensing may be achieved as compared to conventional techniques that simply employ blanking periods during the time a near-field T-wave is expected to appear in the ventricular channel.

As represented by block 710, in the event a QRS complex was not detected during the third time period 604C, the event detector 216 may continue its detection operations. For example, the cardiac device may revert to normal ventricular sensing (e.g., using a fixed threshold or automatic sensitivity control). Thus, a lower sensitivity threshold may be employed to enable more effective detection of QRS complexes, any cardiac signals that may indicate ventricular fibrillation, or any other signals of interest. An example of such a lower sensitivity threshold is represented by upper and lower boundaries of the illustrated dashed line (e.g., line segment 614). As mentioned above, this threshold may be defined just above the noise floor of the ventricular channel or in some other manner to increase the sensitivity of the detection during this time. Here, it should be appreciated that the continuation of these detection operations may correspond, in the following cardiac cycle, to the detection operations that precede the QRS complex 606 of FIG. 6 (e.g., corresponding to the dashed line 612).

Exemplary Cardiac Device

The following description sets forth an exemplary implantable cardiac device (e.g., a cardiac rhythm management device such as an implantable cardioverter defibrillator, a pacemaker, etc.) that is capable of being used in connection with the various embodiments that are described herein. It is to be appreciated and understood that other cardiac devices, including those that are not necessarily implantable, can be used and that the description below is given, in its specific context, to assist the reader in understanding, with more clarity, the embodiments described herein.

Figure 8:
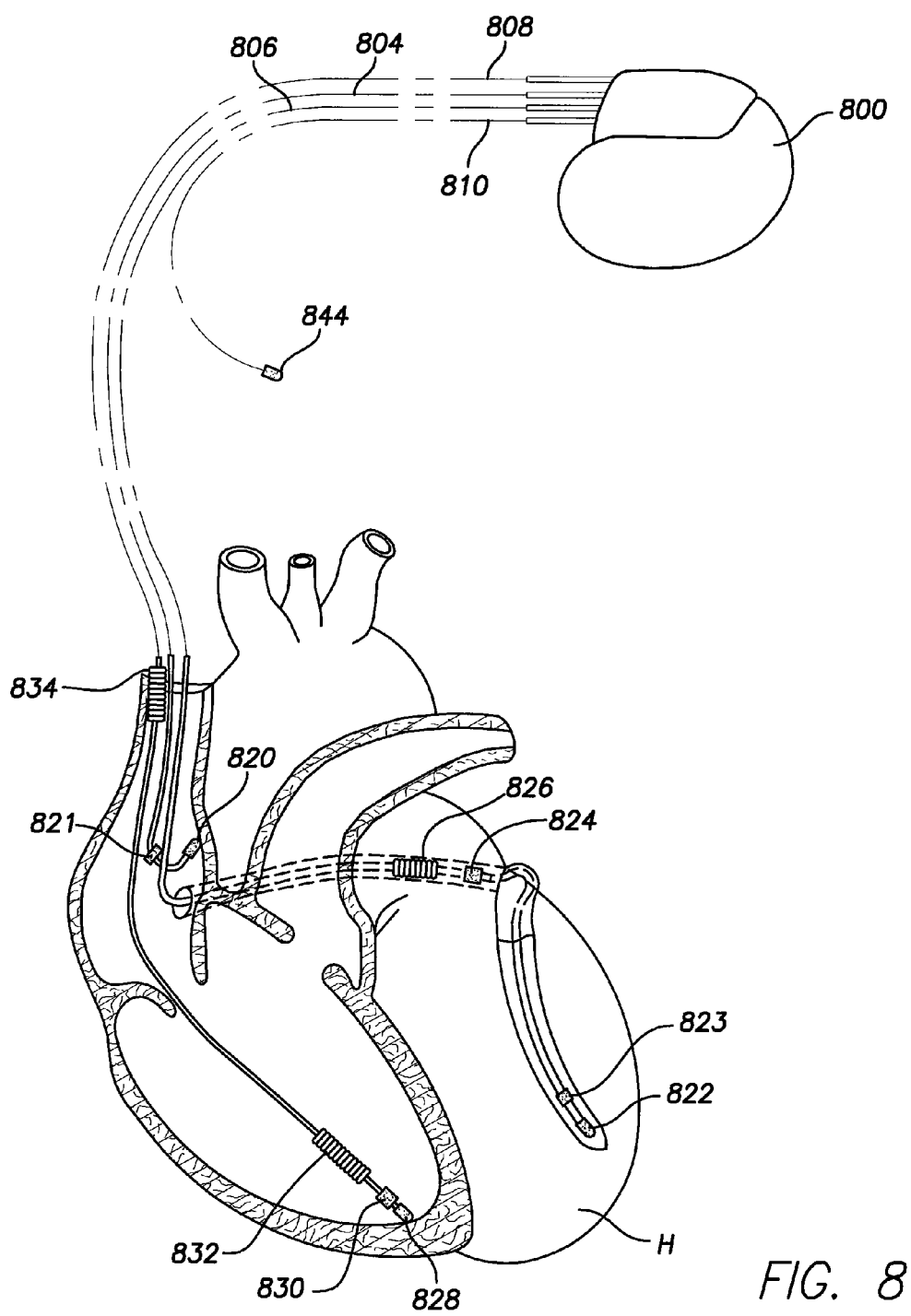
FIG. 8 is a simplified diagram of an embodiment of an implantable cardiac rhythm management device in electrical communication with one or more leads implanted in a patient's heart for sensing conditions in the patient, delivering therapy to the patient, or providing some combination thereof.

FIG. 8 shows an exemplary implantable cardiac device 800 in electrical communication with a patient's heart H by way of three leads 804, 806, and 808, suitable for delivering multi-chamber stimulation and shock therapy. To sense atrial cardiac signals and to provide right atrial chamber stimulation therapy, the device 800 is coupled to an implantable right atrial lead 804 having, for example, an atrial tip electrode 820, which typically is implanted in the patient's right atrial appendage or septum. FIG. 8 also shows the right atrial lead 804 as having an optional atrial ring electrode 821.

To sense left atrial and ventricular cardiac signals and to provide left chamber pacing therapy, the device 800 is coupled to a coronary sinus lead 806 designed for placement in the coronary sinus region via the coronary sinus for positioning one or more electrodes adjacent to the left ventricle, one or more electrodes adjacent to the left atrium, or both. As used herein, the phrase "coronary sinus region" refers to the vasculature of the left ventricle, including any portion of the coronary sinus, the great cardiac vein, the left marginal vein, the left posterior ventricular vein, the middle cardiac vein, the small cardiac vein or any other cardiac vein accessible by the coronary sinus.

Accordingly, an exemplary coronary sinus lead 806 is designed to receive atrial and ventricular cardiac signals and to deliver left ventricular pacing therapy using, for example, a left ventricular tip electrode 822 and, optionally, a left ventricular ring electrode 823; provide left atrial pacing therapy using, for example, a left atrial ring electrode 824; and provide shocking therapy using, for example, a left atrial coil electrode 826 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

The device 800 is also shown in electrical communication with the patient's heart H by way of an implantable right ventricular lead 808 having, in this implementation, a right ventricular tip electrode 828, a right ventricular ring electrode 830, a right ventricular (RV) coil electrode 832 (or other electrode capable of delivering a shock), and a superior vena cava (SVC) coil electrode 834 (or other electrode capable of delivering a shock). Typically, the right ventricular lead 808 is transvenously inserted into the heart H to place the right ventricular tip electrode 828 in the right ventricular apex so that the RV coil electrode 832 will be positioned in the right ventricle and the SVC coil electrode 834 will be positioned in the superior vena cava. Accordingly, the right ventricular lead 808 is capable of sensing or receiving cardiac signals, and delivering stimulation in the form of pacing and shock therapy to the right ventricle.

The device 800 is also shown in electrical communication with a lead 810 including one or more components 844 such as a physiologic sensor. The component 844 may be positioned in, near or remote from the heart.

It should be appreciated that the device 800 may connect to leads other than those specifically shown. In addition, the leads connected to the device 800 may include components other than those specifically shown. For example, a lead may include other types of electrodes, sensors or devices that serve to otherwise interact with a patient or the surroundings.

Figure 9:
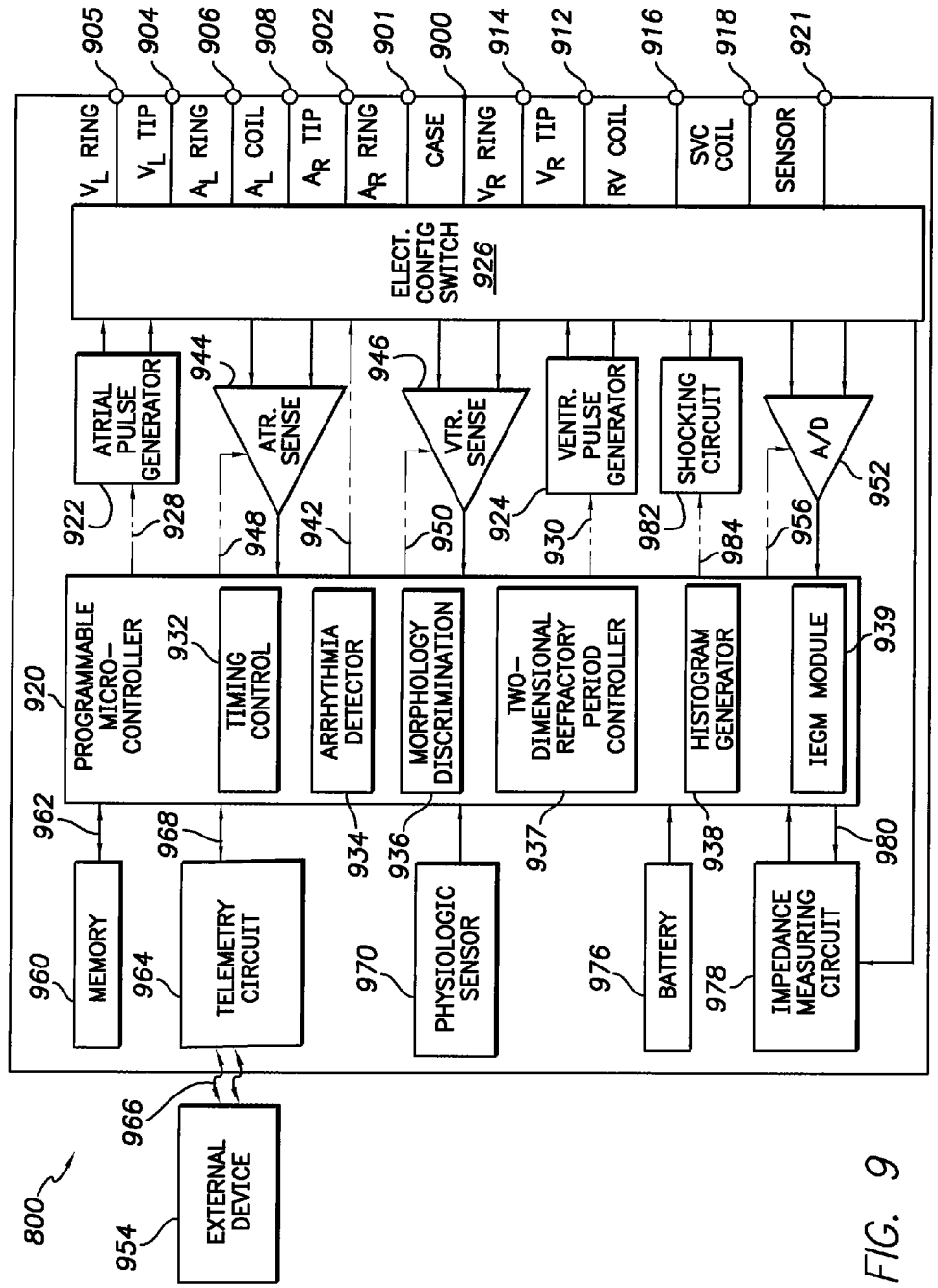
FIG. 9 is a simplified functional block diagram of an embodiment of an implantable cardiac device, illustrating basic elements that may be configured to sense conditions in the patient, deliver therapy to the patient, or provide some combination thereof.

FIG. 9 depicts an exemplary, simplified block diagram illustrating sample components of the device 800. The device 800 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

Housing 900 for the device 800 is often referred to as the "can", "case" or "case electrode", and may be programmably selected to act as the return electrode for all "unipolar" modes. The housing 900 may further be used as a return electrode alone or in combination with one or more of the coil electrodes 826, 832 and 834 for shocking purposes. Housing 900 further includes a connector (not shown) having a plurality of terminals 901, 902, 904, 905, 906, 908, 912, 914, 916 and 918 (shown schematically and, for convenience, the names of the electrodes to which they are connected are shown next to the terminals). The connector may be configured to include various other terminals (e.g., terminal 921 coupled to a sensor or some other component) depending on the requirements of a given application.

To achieve right atrial sensing and pacing, the connector includes, for example, a right atrial tip terminal (AR TIP) 902 adapted for connection to the right atrial tip electrode 820. A right atrial ring terminal (AR RING) 901 may also be included and adapted for connection to the right atrial ring electrode 821. To achieve left chamber sensing, pacing, and shocking, the connector includes, for example, a left ventricular tip terminal (VL TIP) 904, a left ventricular ring terminal (VL RING) 905, a left atrial ring terminal (AL RING) 906, and a left atrial shocking terminal (AL COIL) 908, which are adapted for connection to the left ventricular tip electrode 822, the left ventricular ring electrode 823, the left atrial ring electrode 824, and the left atrial coil electrode 826, respectively.

To support right chamber sensing, pacing, and shocking, the connector further includes a right ventricular tip terminal (VR TIP) 912, a right ventricular ring terminal (VR RING) 914, a right ventricular shocking terminal (RV COIL) 916, and a superior vena cava shocking terminal (SVC COIL) 918, which are adapted for connection to the right ventricular tip electrode 828, the right ventricular ring electrode 830, the RV coil electrode 832, and the SVC coil electrode 834, respectively.

At the core of the device 800 is a programmable microcontroller 920 that controls the various modes of stimulation therapy. As is well known in the art, microcontroller 920 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 920 includes the ability to process or monitor input signals (data or information) as controlled by a program code stored in a designated block of memory. The type of microcontroller is not critical to the described implementations. Rather, any suitable microcontroller 920 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 9 also shows an atrial pulse generator 922 and a ventricular pulse generator 924 that generate pacing stimulation pulses for delivery by the right atrial lead 804, the coronary sinus lead 806, the right ventricular lead 808, or some combination of these leads via an electrode configuration switch 926. It is understood that in order to provide stimulation therapy in each of the four chambers of the heart, the atrial and ventricular pulse generators 922 and 924 may include dedicated, independent pulse generators, multiplexed pulse generators, or shared pulse generators. The pulse generators 922 and 924 are controlled by the microcontroller 920 via appropriate control signals 928 and 930, respectively, to trigger or inhibit the stimulation pulses.

Microcontroller 920 further includes timing control circuitry 932 to control the timing of the stimulation pulses (e.g., pacing rate, atrio-ventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, etc., as known in the art.

Microcontroller 920 further includes an arrhythmia detector 934. The arrhythmia detector 934 may be utilized by the device 800 for determining desirable times to administer various therapies. The arrhythmia detector 934 may be implemented, for example, in hardware as part of the microcontroller 920, or as software/firmware instructions programmed into the device 800 and executed on the microcontroller 920 during certain modes of operation.

Microcontroller 920 may include a morphology discrimination module 936, a capture detection module 937 and an auto sensing module 938. These modules are optionally used to implement various exemplary recognition algorithms or methods. The aforementioned components may be implemented, for example, in hardware as part of the microcontroller 920, or as software/firmware instructions programmed into the device 800 and executed on the microcontroller 920 during certain modes of operation.

The electrode configuration switch 926 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 926, in response to a control signal 942 from the microcontroller 920, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 944 and ventricular sensing circuits (VTR. SENSE) 946 may also be selectively coupled to the right atrial lead 804, coronary sinus lead 806, and the right ventricular lead 808, through the switch 926 for detecting the presence of cardiac activity in each of the four chambers of the heart. Accordingly, the atrial and ventricular sensing circuits 944 and 946 may include dedicated sense amplifiers, multiplexed amplifiers, or shared amplifiers. Switch 926 determines the "sensing polarity" of the cardiac signal by selectively closing the appropriate switches, as is also known in the art. In this way, the clinician may program the sensing polarity independent of the stimulation polarity. The sensing circuits (e.g., circuits 944 and 946) are optionally capable of obtaining information indicative of tissue capture.

Each sensing circuit 944 and 946 preferably employs one or more low power, precision amplifiers with programmable gain, automatic gain control, bandpass filtering, a threshold detection circuit, or some combination of these components, to selectively sense the cardiac signal of interest. The automatic gain control enables the device 800 to deal effectively with the difficult problem of sensing the low amplitude signal characteristics of atrial or ventricular fibrillation.

The outputs of the atrial and ventricular sensing circuits 944 and 946 are connected to the microcontroller 920, which, in turn, is able to trigger or inhibit the atrial and ventricular pulse generators 922 and 924, respectively, in a demand fashion in response to the absence or presence of cardiac activity in the appropriate chambers of the heart. Furthermore, as described herein, the microcontroller 920 is also capable of analyzing information output from the sensing circuits 944 and 946, a data acquisition system 952, or both. This information may be used to determine or detect whether and to what degree tissue capture has occurred and to program a pulse, or pulses, in response to such determinations. The sensing circuits 944 and 946, in turn, receive control signals over signal lines 948 and 950, respectively, from the microcontroller 920 for purposes of controlling the gain, threshold, polarization charge removal circuitry (not shown), and the timing of any blocking circuitry (not shown) coupled to the inputs of the sensing circuits 944 and 946 as is known in the art.

For arrhythmia detection, the device 800 utilizes the atrial and ventricular sensing circuits 944 and 946 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 934 of the microcontroller 920 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 952. The data acquisition system 952 is configured (e.g., via signal line 956) to acquire intracardiac electrogram ("IEGM") signals or other signals, convert the raw analog data into a digital signal, and store the digital signals for later processing, for telemetric transmission to an external device 954, or both. For example, the data acquisition system 952 may be coupled to the right atrial lead 804, the coronary sinus lead 806, the right ventricular lead 808 and other leads through the switch 926 to sample cardiac signals across any pair of desired electrodes.

The data acquisition system 952 also may be coupled to receive signals from other input devices. For example, the data acquisition system 952 may sample signals from a physiologic sensor 970 or other components shown in FIG. 9 (connections not shown).

The microcontroller 920 is further coupled to a memory 960 by a suitable data/address bus 962, wherein the programmable operating parameters used by the microcontroller 920 are stored and modified, as required, in order to customize the operation of the device 800 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart H within each respective tier of therapy. One feature of the described embodiments is the ability to sense and store a relatively large amount of data (e.g., from the data acquisition system 952), which data may then be used for subsequent analysis to guide the programming of the device 800.

Advantageously, the operating parameters of the implantable device 800 may be non-invasively programmed into the memory 960 through a telemetry circuit 964 in telemetric communication via communication link 966 with the external device 954, such as a programmer, transtelephonic transceiver, a diagnostic system analyzer or some other device. The microcontroller 920 activates the telemetry circuit 964 with a control signal (e.g., via bus 968). The telemetry circuit 964 advantageously allows intracardiac electrograms and status information relating to the operation of the device 800 (as contained in the microcontroller 920 or memory 960) to be sent to the external device 954 through an established communication link 966.

The device 800 can further include one or more physiologic sensors 970. In some embodiments the device 800 may include a "rate-responsive" sensor that may provide, for example, information to aid in adjustment of pacing stimulation rate according to the exercise state of the patient. One or more physiologic sensors 970 (e.g., a pressure sensor) may further be used to detect changes in cardiac output, changes in the physiological condition of the heart, or diurnal changes in activity (e.g., detecting sleep and wake states). Accordingly, the microcontroller 920 responds by adjusting the various pacing parameters (such as rate, A-V Delay, V-V Delay, etc.) at which the atrial and ventricular pulse generators 922 and 924 generate stimulation pulses.

While shown as being included within the device 800, it is to be understood that a physiologic sensor 970 may also be external to the device 800, yet still be implanted within or carried by the patient. Examples of physiologic sensors that may be implemented in conjunction with the device 800 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

The one or more physiologic sensors 970 may optionally include one or more of components to help detect movement (via, e.g., a position sensor or an accelerometer) and minute ventilation (via an MV sensor) in the patient. Signals generated by the position sensor and MV sensor may be passed to the microcontroller 920 for analysis in determining whether to adjust the pacing rate, etc. The microcontroller 920 may thus monitor the signals for indications of the patient's position and activity status, such as whether the patient is climbing up stairs or descending down stairs or whether the patient is sitting up after lying down.

The device 800 additionally includes a battery 976 that provides operating power to all of the circuits shown in FIG. 9. For a device 800 which employs shocking therapy, the battery 976 is capable of operating at low current drains (e.g., preferably less than 10 μA) for long periods of time, and is capable of providing high-current pulses (for capacitor charging) when the patient requires a shock pulse (e.g., preferably, in excess of 2 A, at voltages above 200 V, for periods of 10 seconds or more). The battery 976 also desirably has a predictable discharge characteristic so that elective replacement time can be detected. Accordingly, the device 800 preferably employs lithium or other suitable battery technology.

The device 800 can further include magnet detection circuitry (not shown), coupled to the microcontroller 920, to detect when a magnet is placed over the device 800. A magnet may be used by a clinician to perform various test functions of the device 800 and to signal the microcontroller 920 that the external device 954 is in place to receive data from or transmit data to the microcontroller 920 through the telemetry circuit 964.

The device 800 further includes an impedance measuring circuit 978 that is enabled by the microcontroller 920 via a control signal 980. The known uses for an impedance measuring circuit 978 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 800 has been implanted; measuring stroke volume; and detecting the opening of heart valves, etc. The impedance measuring circuit 978 is advantageously coupled to the switch 926 so that any desired electrode may be used.

In the case where the device 800 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 920 further controls a shocking circuit 982 by way of a control signal 984. The shocking circuit 982 generates shocking pulses of low (e.g., up to 0.5 J), moderate (e.g., 0.5 J to 10 J), or high energy (e.g., 11 J to 40 J), as controlled by the microcontroller 920. Such shocking pulses are applied to the patient's heart H through, for example, two shocking electrodes and as shown in this embodiment, selected from the left atrial coil electrode 826, the RV coil electrode 832 and the SVC coil electrode 834. As noted above, the housing 900 may act as an active electrode in combination with the RV coil electrode 832, as part of a split electrical vector using the SVC coil electrode 834 or the left atrial coil electrode 826 (i.e., using the RV electrode as a common electrode), or in some other arrangement.

Cardioversion level shocks are generally considered to be of low to moderate energy level (so as to minimize pain felt by the patient), be synchronized with an R-wave, pertain to the treatment of tachycardia, or some combination of the above. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 920 is capable of controlling the synchronous or asynchronous delivery of the shocking pulses.

As mentioned above, a device such as the device 800 may include several components that provide cardiac signal acquisition functionality as taught herein. For example, one or more of the switch 926, the sense circuits 944 and 946, the impedance measuring circuit 978, the physiologic sensors 970, and the data acquisition system 952 may acquire cardiac signals that are used in the operations discussed above. The data described above may be stored in the data memory 960.

The microcontroller 920 (e.g., a processor providing signal processing functionality) also may implement or support at least a portion of the functionality discussed herein. For example, an IEGM module 939 may generate IEGM data representative of sensed cardiac signals. In addition, a histogram generator 938 may generate histograms as discussed herein. Also, a two-dimensional refractory period controller 937 may perform various functions relating to defining one or more refractory periods and facilitating detection of cardiac events using the refractory period(s). In some implementations the morphology discrimination component 936 may be used to identify certain cardiac events for defining the refractory period(s). Also, the timing control component 932 may provide timing in conjunction with defining and using the refractory period(s).

It should be appreciated that various modifications may be incorporated into the disclosed embodiments based on the teachings herein. For example, the structure and functionality taught herein may be incorporated into types of devices other than the specific types of devices described above. In addition, a two-dimensional refractory period may be defined in various ways (e.g., including different time periods and associated thresholds). In addition, a two-dimensional refractory period may be defined based on different types of information. A variety of techniques may be used to acquire such information. For example, the acquisition of information for the two-dimensional refractory period definition process may involve an amplitude-based detection scheme, one or more threshold-based histograms, morphology discrimination, or some other suitable scheme.

It should be appreciated from the above that the various structures and functions described herein may be incorporated into a variety of apparatuses (e.g., a cardiac rhythm management device, a lead, a monitoring device, etc.) and implemented in a variety of ways. Different embodiments of such an apparatus may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may send raw data or processed data to an external device that then performs the necessary processing.

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to an element herein using a designation such as "first," "second," and so forth does not generally limit the quantity or order of those elements. Rather, these designations may be used herein as a convenient method of distinguishing between two or more different nodes. Thus, a reference to first and second sets does not mean that only two sets may be employed there or that the first set must precede the second set in some manner. Also, unless stated otherwise a set of elements may comprise one or more elements.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad inventive scope thereof. In view of the above it will be understood that the teachings herein are intended to cover any changes, adaptations or modifications which are within the scope of the disclosure as defined by any claims associated herewith.

What is claimed is:

1. A method of detecting cardiac events, comprising:
acquiring cardiac signals sensed in a first chamber;
detecting at least one of a P-wave and a retrograde P-wave associated with the acquired cardiac signals based on detection parameters associated with a refractory period, wherein the detection parameters comprise at least one temporal characteristic and at least one threshold level;
adapting the at least one temporal characteristic based on a temporal characteristic of at least one of a far-field T-wave and a far-field ventricular complex sensed in the first chamber; and
adapting the at least one threshold level based on amplitude characteristics of the at least one of the far-field T-wave and the far-field ventricular complex sensed in the first chamber.

2. The method of claim 1, further comprising rejecting, based on the detection parameters, a far-field T-wave and/or a far-field QRS complex.

3. The method of claim 1, further comprising adapting the at least one threshold level to be higher than a level associated with T-waves and lower than a level associated with P-waves.

4. The method of claim 1, further comprising adapting the at least one threshold level based on at least one amplitude associated with at least one of the group consisting of: a P-wave, a retrograde P-wave, a far-field T-wave, and a far-field QRS complex.

5. The method of claim 1, further comprising adapting the at least one temporal characteristic to correspond to at least one width associated with at least one of the group consisting of: a far-field T-wave and a far-field QRS complex.

6. The method of claim 1, wherein the at least one temporal characteristic and the at least one threshold level are repeatedly adapted based on the temporal and amplitude characteristics of the other cardiac signals.

7. The method of claim 1, wherein the detection parameters define a blanking interval.

8. The method of claim 1, further comprising generating a histogram based on the temporal and amplitude characteristics of the other cardiac signals, wherein the at least one temporal characteristic and the at least one threshold level of the refractory period are adapted based on the histogram.

9. An apparatus for detecting cardiac events, comprising:
a sense circuit configured to acquire cardiac signals sensed in a first chamber;
an event detector configured to detect at least one cardiac event associated with the acquired cardiac signals based on detection parameters associated with a refractory period, wherein the detection parameters comprise at least one temporal characteristic and at least one threshold level; and
a detection parameter adapter configured to adapt the at least one temporal characteristic based on a temporal characteristic of at least one of a far-field T-wave and a far-field ventricular complex sensed in the first chamber and the at least one threshold level based on amplitude characteristics of the at least one of the far-field T-wave and the far-field ventricular complex sensed in the first chamber.

10. The apparatus of claim 9, wherein the at least one cardiac event comprises a P-wave, a retrograde P-wave, or atrial fibrillation.

11. The apparatus of claim 10, wherein the event detector is further configured to reject, based on the detection parameters, a far-field T-wave and/or a far-field QRS complex.

12. The apparatus of claim 10, wherein the detection parameter adapter is further configured to adapt the at least one threshold level to be higher than a level associated with T-waves and lower than a level associated with P-waves.

13. The apparatus of claim 10, wherein the detection parameter adapter is further configured to:
adapt the at least one threshold level based on at least one amplitude associated with at least one of the group consisting of: a P-wave, a retrograde P-wave, a far-field T-wave, and a far-field QRS complex; and
adapt the at least one temporal characteristic to correspond to at least one width associated with at least one of the group consisting of: a far-field T-wave and a far-field QRS complex.

14. An implantable system for detecting cardiac events, comprising:
means for acquiring cardiac signals sensed in a first chamber;
means for detecting at least one cardiac event associated with the acquired cardiac signals based on detection parameters associated with a refractory period, wherein the detection parameters comprise at least one temporal characteristic and at least one threshold level; and
means for adapting the at least one temporal characteristic based on a temporal characteristic of at least one of a far-field T-wave and a far-field ventricular complex sensed in the first chamber and for adapting the at least one threshold level based on an amplitude characteristics of the at least one of the far-field T-wave and the far-field ventricular complex sensed in the first chamber.

* * * * *